United States Patent
Tsujii

(10) Patent No.: US 7,315,606 B2
(45) Date of Patent: Jan. 1, 2008

(54) X-RAY IMAGING APPARATUS AND ITS CONTROL METHOD

(75) Inventor: Osamu Tsujii, Ohta-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/107,965

(22) Filed: Apr. 18, 2005

(65) Prior Publication Data

US 2005/0238141 A1    Oct. 27, 2005

(30) Foreign Application Priority Data

Apr. 21, 2004    (JP)    ............................. 2004-125831

(51) Int. Cl.
*G01N 23/00* (2006.01)

(52) U.S. Cl. ........................................... 378/20; 378/4

(58) Field of Classification Search ................ 378/10, 378/20, 4, 207, 205, 208–209, 8, 13–14
See application file for complete search history.

(56) References Cited

U.S. PATENT DOCUMENTS

| | | | | |
|---|---|---|---|---|
| 3,670,163 | A | 6/1972 | Lajus | 250/50 |
| 5,668,845 | A * | 9/1997 | Migita | 378/4 |
| 6,061,422 | A * | 5/2000 | Miyazaki et al. | 378/15 |
| 6,307,910 | B1 | 10/2001 | Acharya et al. | 378/4 |
| 6,470,068 | B2 * | 10/2002 | Cheng | 378/20 |
| 6,480,560 | B2 | 11/2002 | Hsieh | 378/8 |
| 6,944,261 | B2 * | 9/2005 | Adachi et al. | 378/20 |
| 2003/0123603 | A1 | 7/2003 | Suzuki | 378/4 |
| 2003/0190010 | A1 | 10/2003 | Tsujii | 378/23 |
| 2003/0202631 | A1 | 10/2003 | Ohishi et al. | 378/62 |
| 2005/0147285 | A1 | 7/2005 | Tago et al. | 382/130 |
| 2005/0226486 | A1 | 10/2005 | Tsujii | 382/132 |

FOREIGN PATENT DOCUMENTS

| | | |
|---|---|---|
| EP | 1 302 164 A2 | 4/2003 |
| JP | 06 277209 A | 10/1994 |
| JP | 2001-224588 | 8/2001 |
| JP | 3347765 | 9/2002 |
| JP | 2002-355241 | 12/2002 |

OTHER PUBLICATIONS

Patent Abstract of Japan, vol. 1995, No. 1 (JP 06-277209-A).
L. A. Feldkamp et al., *Practical cone-beam algorithm*, J. Opt Soc. Of Am., A/vol. 1, No. 6, pp. 612-619, Jun. 1984.

* cited by examiner

*Primary Examiner*—Hoon Song
(74) *Attorney, Agent, or Firm*—Fitzpatrick, Cella, Harper & Scinto

(57) ABSTRACT

In an X-ray imaging apparatus, which has a radiation source for generating radiation, and a detector for detecting the amount of radiation of the radiation, a subject is relatively rotated with respect to radiation which is radiated from the radiation source in the direction of the detector, and radiation amount data for image reconstruction is acquired in a predetermined rotation section. At this time, a desired observation direction perpendicular to the rotation axis in association with the subject is designated, and the position of the predetermined rotation section is determined on the basis of the designated observation direction.

6 Claims, 4 Drawing Sheets

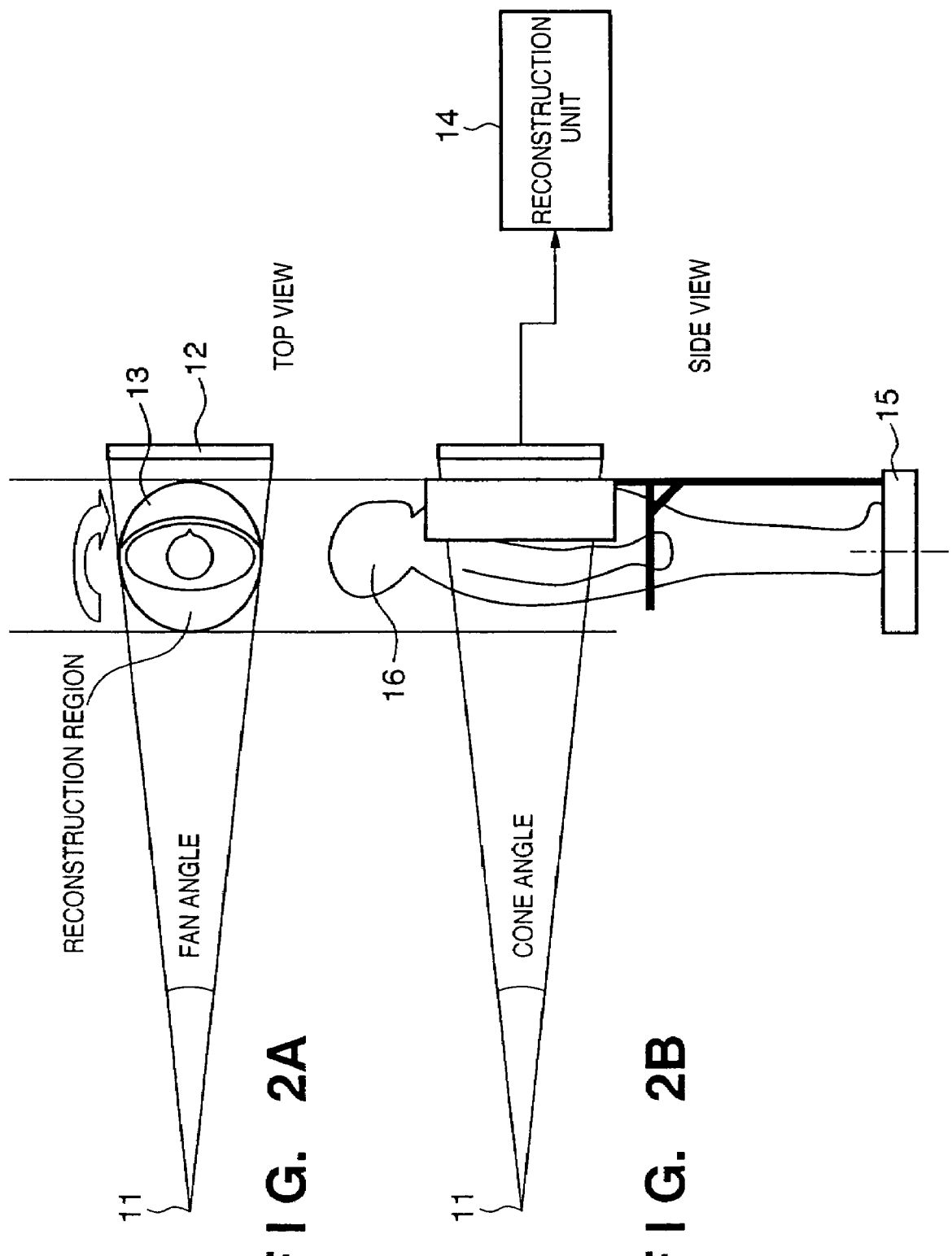

X-RAY IMAGING APPARATUS AND ITS CONTROL METHOD

FIELD OF THE INVENTION

The present invention relates to an X-ray imaging technique for imaging a radiation distribution in a subject using radiation such as an X-ray CT apparatus for sensing an image using radiation such as X-rays or the like.

BACKGROUND OF THE INVENTION

Conventionally, an X-ray CT apparatus which irradiates a subject with X-rays, detects X-rays transmitted through or scattered by the subject using an X-ray detector, and forms a fluoroscopic image, tomosynthesis, or three-dimensional (3D) image on the basis of this X-ray detection output (the number of photons of X-rays) is known. As such X-ray CT apparatus, a cone beam CT apparatus has been developed. In a normal X-ray CT apparatus, an X-ray beam is limited in the Z-direction, and is called a fan beam. However, cone beam CT (CBCT) uses an X-ray beam which also spreads in the Z-direction, and for this reason is called a cone beam.

In CT, a half-scanning technique that scans through "180°+fan angle" is known. In this half-scanning technique, when a gantry which mounts an X-ray generation source and X-ray detector is not located at a predetermined rotation position (one of 0°, 90°, 180°, and 270°), the control waits until the gantry reaches this predetermined rotation position, and then starts measurement. For this reason, the actual measurement start time is indefinite and typically does not coincide with a time planned for starting measurement, resulting in poor time-setting precision. That is, in order to obtain a tomosynthesis for a subject to be examined, the subject is inserted into an opening of the gantry, which is rotated around the subject through 360°, and measurement (imaging) starts from a predetermined measurement start angle (for example, one of 0°, 90°, 180°, and 270° detected by an angle detector). An image processing apparatus performs image reconstruction required to obtain a tomosynthesis using measurement data obtained in this way. The image reconstruction is done under the condition that data measured by a scanner starts from the predetermined angle (an angle as one of 0°, 90°, 180°, and 270°).

This "start" is an initial 0° equivalent position in the sense that the image reconstruction in the half-scanning method reconstructs an image using projection data for what is thought of as 0° to 180°. This 0° equivalent position, as described above, is actually one of four absolute angles, i.e., 0°, 90°, 180°, and 270°, as the absolute angle of orientation of the gantry.

A technique for implementing such process is proposed by Japanese Patent No. 03347765 (to be referred to as reference 1 hereinafter). According to reference 1, measurement data appended with the detection angle of the gantry is obtained, and a data start angle position (0° to 360° or 0° to 180°) and data for 360° or 180° turn from this start angle position can be determined from the angle appended to the measurement data. In this way, the measurement start position can be freely set at an angle other than 0°, 90°, 180°, and 270°. Furthermore, even when an angle θ which does not reach each of the 0°, 90°, 180°, and 270° positions (0°<θ<90°, 90°<θ<180°, 180°<θ<270°, 270°<θ<360°) is set, that measurement start position can be set as a measurement start position of data for 360° or 180° turn as long as the measurement starts.

On the other hand, Japanese Patent Laid-Open No. 2001-224588 (to be referred to as reference 2 hereinafter) discloses a technique for imaging a body part (heart) of a patient having cyclic motions using a slice imaging system in association with heart imaging using half-scanning. An axial "half-scan" is segmented into N sectors (N being a positive integer which is equal to or larger than 2). Note that "half-scanning" involves executing a scan over a view angle range equal to an angle obtained by adding one fan angle to 180°. According to reference 2, image data that represent at least one half-scan is acquired by acquiring image data corresponding to each of N sectors in a corresponding heartbeat cycle of the patient for at least N heartbeat cycles. In this known technique, only one sector is acquired per heartbeat cycle. When the imaging system is a multi-slice imaging system, only one sector for each slice is acquired per heartbeat cycle. Since sectors acquired during one heartbeat cycle are acquired in a relatively short period of time in substantially the same parts of these heartbeat cycles, the sectors being combined are ones which have undergone short scans and are obtained from such parts in different heartbeat cycles, thus reducing motion artifacts in the final image. Note that "substantially the same parts of the heartbeat cycles" means that since the positions of a heart in these parts of the heartbeat cycles are similar and have no difference, a reconstructed image important for diagnosis and medical purpose is free from deterioration independently of the difference in position of the heart. A step of gate-driving a radiation source and a step of acquiring sectors of image data are repeated until image data that represent at least a half-scan of one image slice are acquired.

Furthermore, according to Japanese Patent Laid-Open No. 2002-355241 (to be referred to as reference 3 hereinafter), in imaging using half-scanning, an artifact resulting from the motion of a subject is introduced as a maximum mismatch level present in neighboring projection views in CT data set. For example, full scanning typically assumes that a mismatch from the start to the end of scanning is the worst case possible. Upon scanning a subject making recursive motions (which are not always truly cyclic), when the subject has approximately the same motion states at the beginning and the end of scanning, a motion artifact is minimized. That is, it is known that a motion artifact is minimized when the motion cycle precisely matches the cycle of the gantry speed with respect to half-scanning and full scanning. In order to minimize a motion artifact, it is proposed to determine a start projection view after a plurality of projection views are acquired. That is, a difference between the first and the last views used in reconstruction is determined, and a view that minimizes the difference is selected as the start view. For example, the start angle of half-scanning that minimizes motion-induced artifacts is determined by difference projection.

The techniques proposed by references 1 to 3 above reduce generation of artifacts due to subject motions and patient heartbeats by determining data corresponding to an appropriate half-scan from data for one rotation obtained by X-ray imaging and using the determined data in reconstruction. For this purpose, the gantry must make one or more rotations to obtain half-scan data. On the other hand, since the imaging time is preferably short in terms of reducing the burden on a patient and reducing the influence of body motion errors, a measure for increasing the rotation speed of the gantry must be taken.

On the other hand, in CBCT, when a large organ such as lungs or the like is to be imaged by a single scan, since the cone angle is limited to a small value so as not to cause reconstruction errors, the FDD (focus detector distance) must be set to be as large as about 2.5 m. In this case, the following problems are posed:

(1) The gantry becomes bulky, and cannot be carried into a room in the case of a recumbent position CT which is currently distributed. Since a large centrifugal force is generated upon rotation, a high-speed imaging system cannot be adopted.

(2) When a type that rotates a subject (subject rotation type) is adopted, the scan time ranges from 5 to 10 sec/rotation.

Especially, in the subject rotation type, use of half-scanning with a shorter scanning time is strongly demanded so as to reduce errors caused by body motion. In order to meet a requirement of reducing the patient's exposure to X-rays, a technique for executing half-scan imaging itself at a suited timing is required in place of the conventional method that selects half-scan data from one-rotation data.

SUMMARY OF THE INVENTION

The present invention has been made in consideration of the aforementioned problems, and has as its object to perform suitable control of the imaging timing to obtain half-scan data required to reconstruct an image, and for example, to acquire data suited to image reconstruction even by just one half-scan.

According to one aspect of the present invention, there is provided an X-ray imaging apparatus, which has a radiation source for generating radiation, and a detector for detecting an amount of radiation of the radiation. The apparatus also comprises a rotation unit adapted to effect relative rotation of a subject with respect to radiation which is radiated from the radiation source in a direction of the detector. Also provided is a designation unit adapted to designate a desired observation direction perpendicular to a rotation axis of the rotation unit, as well as determination means for determining an imaging start position of a half-scan imaging on the basis of the observation direction designated by said designation unit, and reconstruction means for reconstructing an image using radiation amount data acquired by the half-scan imaging started from the imaging start position. The determination means determine a rotation position where the observation direction is perpendicular to a radiation direction of radiation from the radiation source as the imaging start position.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 2A and 2B are views for explaining the arrangement of an X-ray imaging apparatus according to the preferred embodiment of the present invention;

DETAILED DESCRIPTION OF THE PREFERRED EMBODIMENTS

The preferred embodiments of the present invention will now be described in detail in accordance with the accompanying drawings.

Figure 1A:
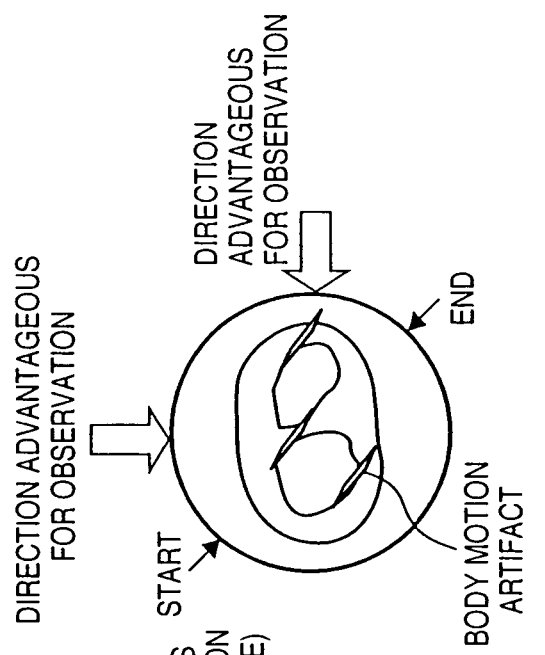
FIGS. 1A to 1C are views for explaining the concept of an embodiment of the present invention.
Figure 1B:
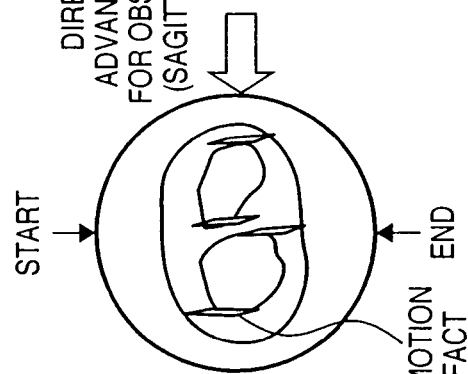
Figure 1C:
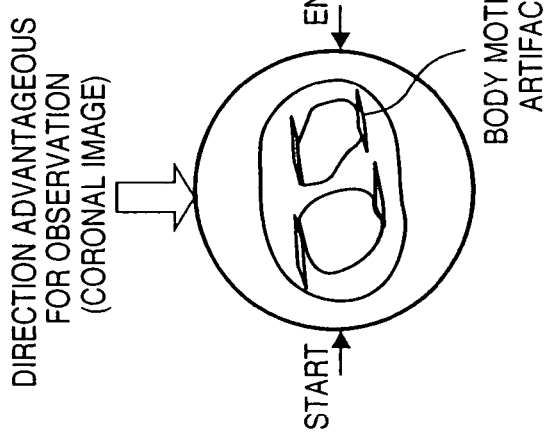

FIGS. 1A to 1C are views for explaining the concept of an embodiment of the present invention. FIGS. 1A to 1C show a chest axial image, a data acquisition start position (START) and end position (END) in half-scanning (180°+fan angle), and a suitable observation direction associated with a tomosynthesis which is reconstructed from data obtained by half-scanning, and is parallel to the body axis. When body motion has occurred in a half-scan, a data mismatch in the START and END directions becomes conspicuous, and linear artifacts are generated in a direction parallel to a line that connects the START and END positions. Taking FIG. 1A as an example, linear artifacts that run in the lateral direction are generated. In the case of FIG. 1B, linear artifacts that run in the up-and-down direction (in the drawing figure) are generated. Also, in the case of FIG. 1C, linear artifacts that run in the oblique direction are generated.

When the phenomenon "of linear artifacts" is observed in an axial image, generation of the artifacts in an image does not depend on the half-scanning start positions. That is, only the line directions of artifacts are different depending on the half-scan start position, while the strength of artifacts depends on the magnitude of the body motion. However, artifacts resulting from the body motion on coronal and sagittal images reconstructed from half-scan data do depend on the half-scanning start positions. For example, in a half-scan shown in FIG. 1A, when the body motion has occurred, artifacts as horizontal lines are generated. When these horizontal lines are observed in a sagittal image, they are observed as a high-contrast pattern. However, when these horizontal lines are observed in a coronal image, they are observed as a low-contrast pattern. This is because an image is generated to have a certain thickness and is observed upon generating sagittal and coronal images, and as a result the contrast changes by averaging for the observation thickness. That is, in the case of FIG. 1A, addition is made in the START-END direction in a sagittal image, and so artifacts are emphasized. On the other hand, when addition is made in a direction perpendicular to the START-END direction in a coronal image, artifacts are attenuated. Likewise, in half-scans shown in FIGS. 1B and 1C, directions that lower the contrast of artifacts resulting from the body motion exist. That is, if the observation direction is determined, the half-scan start position (START) and end position (END) suited to the observation direction are determined.

Generally speaking, when the half scan section is determined so that the direction of a line segment that connects the half scan start position (START) and end position (END) is perpendicular to the observation direction, the contrast of artifacts can be reduced in an image in that observation direction. That is, when the rotation position where the observation direction is perpendicular to the radiation direction of radiation from a radiation source is set as the start position of the half scan section, the contrast of artifacts in an image in the designated observation direction is reduced. As shown in FIG. 1C, when the contrast of artifacts is to be reduced in an image from two observation directions, the half scan section can be set so that the direction of the line segment that connects the half scan start position (START) and end position (END) is perpendicular to a line segment that bisects an angle defined by these two observation directions. That is, a rotation position where the direction that bisects the angle defined by designated two observation directions is perpendicular to the radiation direction of radiation from the radiation source can be set as the half scan start position. Also, when three or more observation directions are designated, two end observation directions can be handled as the above two directions. By determining the half scan position by the aforementioned method, observation directions other than coronal and sagittal images can be coped with.

The observation direction and radiation direction are defined as follows. The observation direction can be determined by the direction of a surface of a breast plate 13 fixed to a turn table 15, as will be described later using FIGS. 2A and 2B. When the breast plate 13 is used, a direction perpendicular to the surface where a breast contacts is sagittal, and a direction parallel to the surface is coronal. The same applies to a back plate used in place of the breast plate. When a contact plate against which the body side surface is pressed is provided to the turn table 15, a direction perpendicular to the surface of the contact plate is coronal. The radiation direction is a direction that connects an X-ray generator 11 and two-dimensional detector 12. The positional relationship between the turn table 15 and breast plate 13 is fixed. Therefore, in this embodiment, a state wherein the surface where a breast contacts of the breast plate 13 faces the X-ray generator 11, as shown in, e.g., FIG. 2A is defined as the rotation angle=0° of the turn table 15 so as to measure a rotation angle. In this case, the direction of a subject faces the front (front surface or back surface) with respect to the X-ray generator 11 when the turn table is located at a 0° or 180° position, and faces the side surface (right or left side surface) when the turn table is located at a 90° or 270° position. That is, the half-scan start and end positions are detected by detecting the rotation angle of the turn table 15.

An X-ray imaging apparatus of this embodiment will be described in detail below.

FIGS. 2A and 2B show an example of the arrangement of the X-ray imaging apparatus according to the preferred embodiment of the present invention. X-rays emitted by the X-ray generator (X-ray focal point) 11 are transmitted through a subject 16, and reach the two-dimensional (2D) detector 12 after they pass through the breast plate 13 and a scattered ray removal grid (not shown). The 2D detector 12 comprises a semiconductor sensor: one pixel size is, e.g., 250×250 μm, and the sensor outer shape size is 43×43 cm. In this case, the number of pixels is, e.g., 1720×1720 pixels. Data acquired by the 2D detector 12 are transferred to a reconstruction unit 14 and undergo image reconstruction. Note that the fan angle and cone angle are determined by the geometrical layout of the X-ray generator 11 and 2D detector 12. Since this embodiment uses a 2D detector having a square detection surface, the fan angle equals the cone angle.

Figure 3:
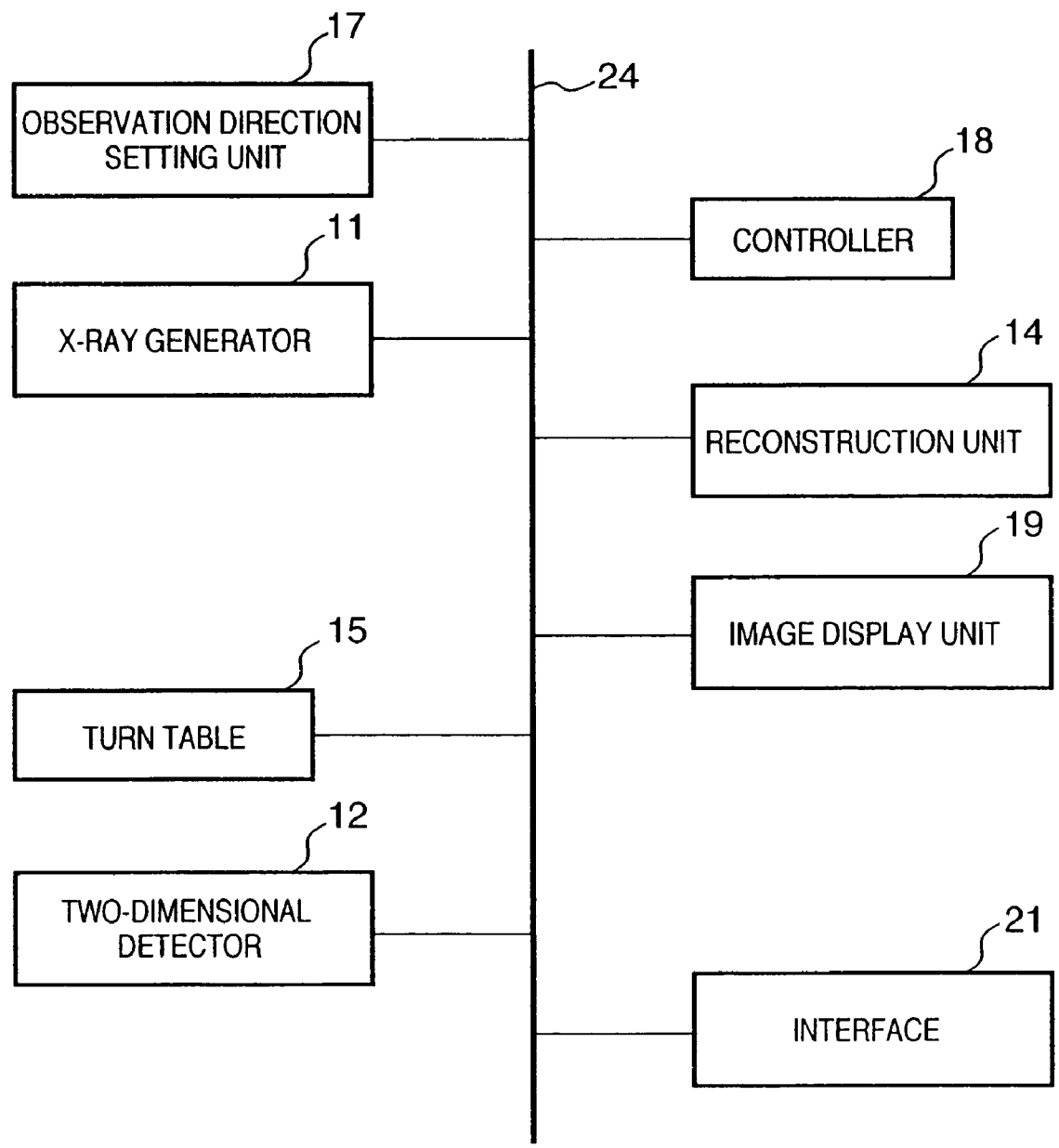
FIG. 3 is a system block diagram of the X-ray imaging apparatus according to the preferred embodiment of the present invention.

FIG. 3 is a block diagram showing the system arrangement of the X-ray imaging apparatus according to this embodiment. In this embodiment, the entire system is implemented by a computer system. However, the present invention is not limited to such specific implementation. A BUS 24 can be considered as an internal bus of the computer, and respective units in the system exchange control signals and data via this BUS 24. A controller 18 includes a CPU and memory (ROM, RAM; not shown), and various processes are implemented when the CPU executes control programs stored in the memory. An interface 21 informs the controller 18 of various instructions from the user. The controller 18 executes various processes in accordance with various instructions from the interface 21. When a direction used to mainly observe a reconstructed image (observation direction) is designated by the interface 21, the designated observation direction is set in an observation direction setting unit 17. When the observation direction setting unit 17 determines the data acquisition start position of half-scanning on the basis of the set observation direction, the interface 21 makes an imaging preparation completion display (not shown). When the user issues an imaging start instruction, the turn table 15 on which the subject 16 is placed begins to rotate in accordance with an instruction from the controller 18. Note that some or all of the processes of the observation direction setting unit 17, interface 21, reconstruction unit 14, and the like may be executed by the CPU of the controller 18.

The controller 18 monitors an encoder signal (not shown) generated from the turn table 15, thus detecting the rotational speed and rotation position of the turn table 15. The controller 18 confirms if the turn table 15 has reached the predetermined speed and angle. When the predetermined speed and the determined data acquisition start position have been reached, the controller 18 sends a signal to the X-ray generator 11 to start X-ray radiation. Note that the encoder signal is also used to determine the integration timing of data.

For example, when an encoder that generates 25000 pulses per revolution of the table is used, and projection data of 1000 views per revolution are acquired, projection data is acquired from the 2D detector 12 every 25 pulses of the encoder signal. The controller 18 counts pulses of the encoder signal to generate an integration signal every 25 pulses, thus counting an X-ray dose that reaches the 2D detector 12. Assume that X-rays are generated continuously in this embodiment. However, the present invention is not limited to this. For example, X-ray pulses may be generated in correspondence with integration periods of the 2D detector 12 on the basis of the encoder signal. Data from the 2D detector 12 are sequentially transferred to the reconstruction unit 14 via the BUS 24. Data transfer continues until the turn table 15 rotates through a predetermined rotation angle, and a predetermined number of views are acquired. Last projection data is acquired immediately after completion of X-ray radiation. In this embodiment, integration and data acquisition (in a narrow sense) are offset by one frame, and (N−1)-th data is A/D-converted into digital data (narrow-sense data acquisition) parallel to integration of N-th radiation. Therefore, upon completion of radiation (integration) for the last image, the last data acquisition is made. The acquired projection data are reconstructed to 3D voxel data by the reconstruction unit 14.

The reconstruction unit 14 executes a pre-process, filter process, and inverse projection process. The pre-process executes, e.g., an offset process, LOG conversion, gain correction, and defect correction. In the filter process, the Ramachandran function or Shepp-Logan function is popularly used. This embodiment also uses such function. Data that have undergone the filter process are inversely projected by the inverse projection process. An algorithm from the filter process to the inverse projection process can be implemented using, for example, the Feldkamp algorithm. Upon completion of the inverse projection process, when a CT cross section image is reconstructed, that cross section image is displayed on an image display unit 19.

Note that the reconstruction algorithm uses the Feldkamp algorithm. However, the present invention is not limited to such specific algorithm. As a reference associated with this Feldkamp algorithm, Feldkamp, Davis, and Kress, "Practical Cone-Beam Algorithm", J. Opt, Soc. Am. Al, 612-619, 1984 is known.

Figure 4:
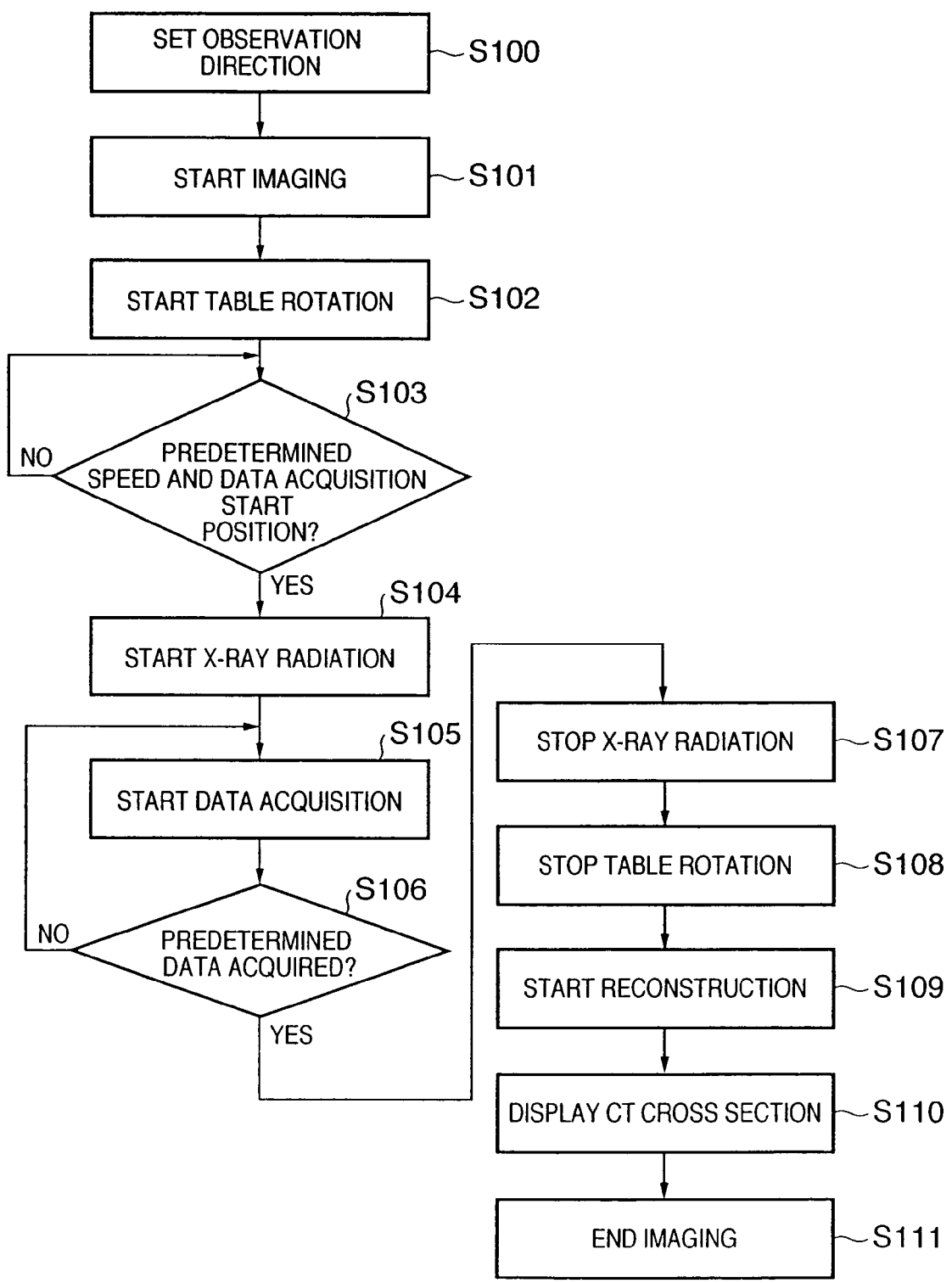
FIG. 4 is a flowchart for explaining the operation of the X-ray imaging apparatus according to the preferred embodiment of the present invention.

The operation of the X-ray imaging apparatus according to this embodiment will be explained below using the flowchart of this embodiment shown in FIG. 4.

The user sets an observation direction via the interface 21 (step S100). Upon setting of the observation direction, the user such as a doctor or the like designates the observation direction directly or designates a body part. When the observation direction is to be directly input, it is selected from three different directions: (1) coronal alone, (2) sagittal alone, and (3) coronal and sagittal. Depending on the observation direction input, the data acquisition start position is determined, as shown in Table 1 below. Also, the observation direction may be input using an angle. For example, 0° can be designated for coronal, 90° can be designated for sagittal, and a desired angle (0° to 90°) between them can be designated.

TABLE 1

| Observation method | Data acquisition start position |
| --- | --- |
| (1) Coronal alone | Start from side surface |
| (2) Sagittal alone | Start from front surface |
| (3) Coronal and sagittal | Start from 45° position from side surface |

Table 2 shows a case wherein the data acquisition start position is determined by designating a body part. A chest image is normally diagnosed using a coronal image in the same direction as general X-ray imaging, and head and abdominal images do not normally have directionality.

TABLE 2

| Body part | Data acquisition start position |
| --- | --- |
| Head | Start from 45° position from side surface |
| Chest | Start from side surface |
| Abdomen | Start from 45° position from side surface |

Note that Tables 1 and 2 are saved as tables in the memory of the controller 18, and which table is to be applied can be set by an instruction from the interface 21. Also, tables like Tables 1 and 2 may be prepared and held in memory for each doctor who requests imaging. In this case, when, for example, a doctor ID is input from the interface 21, a table corresponding to that doctor is selected, and the data acquisition start position is determined in accordance with the designated observation direction or body part.

Next, a patient as the subject 16 is placed on the turn table 15. If an imaging start instruction is input via the interface 21, the turn table 15 begins to rotate in response to an instruction from the controller 18 (steps S101 and S102). The controller 18 monitors an encoder signal (not shown) generated by the turn table 15, and confirms if a predetermined speed and the data acquisition start position (start angle) set as described above have been reached (step S103). Assume that the angle of the turn table 15 is measured to have the state in FIG. 2A as 0°, as described above. Hence, the start angle upon starting imaging from the front surface is 0° (or 180°), that upon starting imaging from the side surface is 90° (or 270°), and that upon starting imaging from the 45° position from the side surface is 45° (or 135°, 225°, or 315°). If the predetermined speed and start angle have been reached, a signal is sent to the X-ray generator 11 to start X-ray radiation (step S104). As described above, this encoder signal is also used to determine the integration timing of data. This embodiment uses an encoder that generates 25000 pulses per revolution of the table is used, and acquires projection data of 1000 views per revolution. Hence, projection data is acquired from the 2D detector 12 every 25 pulses of the encoder signal. The controller 18 counts pulses of the encoder signal to generate an integration signal every 25 pulses, thus counting an X-ray dose that reaches the 2D detector 12 (step S105). Assume that X-rays are generated continuously in this embodiment. However, the present invention is not limited to this. For example, X-ray pulses may be generated in correspondence with integration periods of the 2D detector 12 on the basis of the encoder signal.

Data from the 2D detector 12 are sequentially transferred to the reconstruction unit 14 via the BUS 24. Data transfer continues until the turn table 15 rotates through a predetermined rotation angle, and a predetermined number of views are acquired (step S106). If the turn table 15 has rotated through the predetermined rotation angle and a predetermined number of views have been acquired, the controller 18 stops X-ray radiation of the X-ray generator 11 (step S107). After that, the controller 18 controls to decelerate the turn table 15 until it stops (step S108).

Last projection data is acquired immediately after completion of X-ray radiation. The controller 18 instructs the reconstruction unit 14 to execute a reconstruction process based on the acquired projection data. Note that this embodiment performs reconstruction for each frame (for one direction image). Hence, if a high-speed reconstruction processing circuit is used, data acquisition and reconstruction can be parallelly done, and reconstruction can be completed nearly simultaneously with completion of data acquisition. Also, reconstruction may start after completion of the overall data acquisition (step S109). Note that the reconstruction unit 14 reconstructs a CT cross section image by the aforementioned process, and displays the reconstructed cross section image on the image display unit, thus ending this process (steps S110 and S111). Note that the cross section image reconstructed in step S109 may be the one from the observation direction set in step S100.

As described above, this embodiment focuses attention on that an observation image which is influenced less by artifacts resulting from a body motion can be provided from a specific observation direction even in half scanning. Hence, in a cone beam CT apparatus, the half scan start position suited to an image observation method is automatically determined. Especially, since an isotropic image can be acquired by CBCT, it is effective to make diagnosis using coronal and sagittal images. Therefore, the half scan start position is controlled depending on whether a coronal or sagittal image is preferentially used, and a scan suited to the preferential image can be achieved.

Note that the data acquisition start position is determined by designating the observation direction or body part in this embodiment. For example, in case of a chest imaging dedicated system, an angle such as 0°, 45°, or 90° may be directly set. In the above embodiment, since the breast plate 13 is fixed to the turn table 15, the rotation position of the turn table 15 is determined with reference to the position of the breast plate 13. In this case, a position where the breast plate 13 faces the radiation source is preferably set as 0°

(front position). For example, when the front position is designated as the data acquisition start position, the position at the beginning of rotation is preferably set so that the rotation position reaches the front position after the turn table begins to rotate and reaches a given speed.

According to the present invention, the imaging timing required to obtain half scan data used to reconstruct an image can be suitably controlled, and data suited to image reconstruction can be acquired by, e.g., one half scan.

Note that the present invention includes a case wherein the invention is achieved by directly or remotely supplying a program of software (a program corresponding to the flowchart shown in the drawing in the embodiment) that implements the functions of the aforementioned embodiments to a system or apparatus, and reading out and executing the supplied program code by a computer of that system or apparatus.

Therefore, the program code itself installed in a computer to implement the functional process of the present invention using the computer implements the present invention. That is, the scope of the claims of the present invention includes the computer program itself for implementing the functional process of the present invention.

In this case, the form of program is not particularly limited, and an object code, a program to be executed by an interpreter, script data to be supplied to an OS, and the like may be used as along as they have the program function.

As a recording medium for supplying the program, for example, a floppy® disk, hard disk, optical disk, magnetooptical disk, MO, CD-ROM, CD-R, CD-RW, magnetic tape, nonvolatile memory card, ROM, DVD (DVD-ROM, DVD-R), and the like may be used.

As another program supply method, the program may be supplied by establishing connection to a home page on the Internet using a browser on a client computer, and downloading the computer program itself of the present invention or a compressed file containing an automatic installation function from the home page onto a recording medium such as a hard disk or the like. Also, the program code that forms the program of the present invention may be segmented into a plurality of files, which may be downloaded from different home pages. That is, the present invention includes a WWW server which makes a plurality of users download a program file required to implement the functional process of the present invention by the computer.

Also, a storage medium such as a CD-ROM or the like, which stores the encrypted program of the present invention, may be delivered to the user, the user who has cleared a predetermined condition may be allowed to download key information that decrypts the program from a home page via the Internet, and the encrypted program may be executed using that key information to be installed on a computer, thus implementing the present invention.

The functions of the aforementioned embodiments may be implemented not only by executing the readout program code by the computer but also by some or all of actual processing operations executed by an OS or the like running on the computer on the basis of an instruction of that program.

Furthermore, the functions of the aforementioned embodiments may be implemented by some or all of actual processes executed by a CPU or the like arranged in a function extension board or a function extension unit, which is inserted in or connected to the computer, after the program read out from the recording medium is written in a memory of the extension board or unit.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-125831 filed on Apr. 21, 2004, which is hereby incorporated by reference herein.

What is claimed is:

1. An X-ray imaging apparatus comprising:
a radiation source for generating X-ray radiation;
a detector for detecting the X-ray radiation to obtain data for reconstructing an image;
a rotation unit adapted to perform relative rotation of a subject with respect to said radiation source and said detector while said detector detects the X-ray radiation;
an interface unit adapted to input an observation direction to observe a CT cross section image perpendicular to a rotation axis of said rotation unit; and
a controller adapted to control said detector to start a half-scan imaging of the subject at a rotation position where direction of the X-ray radiation is perpendicular to the rotation axis of said rotation unit and perpendicular to the observation direction input by said interface unit.

2. The apparatus according to claim 1, wherein said rotation unit rotates the subject.

3. The apparatus according to claim 1, wherein said interface unit makes a user designate a body part, and
the observation direction is decided in accordance with the body part designated via said interface unit.

4. A method of controlling an X-ray imaging apparatus which comprises a radiation source for generating X-ray radiation, a detector for detecting the X-ray radiation to obtain data for reconstructing an image and a rotation unit adapted to perform relative rotation of a subject with respect to the radiation source and the detector while the detector detects the X-ray radiation, said method comprising:
an input step of inputting an observation direction to observe a CT cross section image perpendicular to a rotation axis of the rotation unit via an interface unit; and
a control step of controlling the detector to start a half-scan imaging of the subject at a rotation position where direction of the X-ray radiation is perpendicular to the rotation axis of the rotation unit and perpendicular to the observation direction input by the interface unit.

5. A control program embodied on a computer-readable medium, for making a computer execute a method of controlling an X-ray imaging apparatus according to claim 4.

6. A storage medium storing a control program for making a computer execute a method of controlling an X-ray imaging apparatus according to claim 4.

* * * * *

UNITED STATES PATENT AND TRADEMARK OFFICE
CERTIFICATE OF CORRECTION

PATENT NO. : 7,315,606 B2  Page 1 of 1
APPLICATION NO. : 11/107965
DATED : January 1, 2008
INVENTOR(S) : Osamu Tsujii It is certified that error appears in the above-identified patent and that said Letters Patent is hereby corrected as shown below:

ON COVER PAGE [75]:
Inventor's address, "Ohta-ku (JP)" should read --Tochigi-ken (JP)--

Signed and Sealed this

Twenty-fourth Day of February, 2009

JOHN DOLL
*Acting Director of the United States Patent and Trademark Office*